United States Patent
Grotehusmann et al.

(10) Patent No.: US 7,331,667 B2
(45) Date of Patent: Feb. 19, 2008

(54) IRIS PATTERN RECOGNITION AND ALIGNMENT

(75) Inventors: Ulf Grotehusmann, Oberpframmern (DE); Gerhard Youssefi, Landshut (DE)

(73) Assignee: Bausch Lomb Incorporated, Rochester, NY (US)

( * ) Notice: Subject to any disclaimer, the term of this patent is extended or adjusted under 35 U.S.C. 154(b) by 653 days.

(21) Appl. No.: 10/474,958

(22) PCT Filed: May 10, 2001

(86) PCT No.: PCT/EP01/05354

§ 371 (c)(1),
(2), (4) Date: Apr. 26, 2004

(87) PCT Pub. No.: WO02/087442

PCT Pub. Date: Nov. 7, 2002

(65) Prior Publication Data

US 2004/0169817 A1 Sep. 2, 2004

Related U.S. Application Data

(60) Provisional application No. 60/286,954, filed on Apr. 27, 2001.

(51) Int. Cl.
*A61B 3/10* (2006.01)

(52) U.S. Cl. .................. 351/205; 351/206; 351/246; 351/209

(58) Field of Classification Search ............... 351/205
See application file for complete search history.

(56) References Cited

U.S. PATENT DOCUMENTS

| | | | |
|---|---|---|---|
| 5,740,803 A * | 4/1998 | Gray et al. | 600/407 |
| 6,247,813 B1 * | 6/2001 | Kim et al. | 351/206 |
| 7,146,983 B1 * | 12/2006 | Hohla et al. | 128/898 |

* cited by examiner

*Primary Examiner*—Jessica T Stultz

(57) ABSTRACT

Apparatus and methods are described for aligning diagnostic and therapeutic iris images, via iris pattern recognition, for effecting more accurate laser treatment of the eye. A method for aligning a dilated pupil diagnostic iris image associated with a diagnostic measurement for calculating a laser treatment, with a constricted pupil diagnostic iris image, by identifying an iris landmark that is not identifiable solely between the two images, includes a sequential plurality of diagnostic iris images of varying pupil size such that the iris landmark can be tracked between the two images. The aligned, constricted pupil diagnostic image can then be aligned with a constricted pupil treatment image and the ablation pattern rotated accordingly. Limbal edge detection is used in the diagnostic images to provide pupil center translation information for translational alignment of the laser treatment. An improved aberrometer is disclosed having a variable visible illumination fixation target for controlling pupil size for the diagnostic images. A diagnostic and therapeutic laser eye treatment system is described incorporating the apparatus and method embodiments of the invention.

28 Claims, 3 Drawing Sheets

TYPICAL LANDMARKS

IRIS PATTERN RECOGNITION AND ALIGNMENT

This application is related to PCT EP00/10373.

BACKGROUND OF THE INVENTION

1. Field of the Invention

This invention relates generally to the field of laser vision correction and laser eye surgery, and more specifically to a device, system and methods for alignment of diagnostic and treatment images of the eye for more accurate surgical outcomes and improved patient satisfaction.

2. Description of Related Art

The popularity of photorefractive surgery for the correction or enhancement of vision continues to rise. Techniques such as photorefractive keratotomy (PRK), laser in situ keratomileusis (LASIK), laser epithelial keratomileusis (LASEK) and variations thereof are now commonly used to correct the effects of nearsightedness (myopia), farsightnesses (hyperopia), and astigmatism, in addition to more traditional retinal surgery and other ocular surgical procedures. These vision defects are typically treated by laser ablating the cornea to steepen or flatten it according to its deviation from a geometry that is expected provide normal vision. A topography device such as, e.g., an Orbscan® corneal topographer (Bausch & Lomb/Orbtek, Salt Lake City, Utah) is routinely used to acquire the diagnostic information about the shape and other characteristics of the cornea. A surgeon can then use a laser programmed with this topographic information to appropriately ablate the corneal surface.

Basically, hyperopia and myopia, and astigmatism, are known as lower order aberrations referred to as defocus and cylinder, respectively. It is well known that higher order aberrations in addition to lower order aberrations degrade vision quality. Typical higher order aberrations include spherical aberration, coma, and compound astigmatisms. It is possible to measure these higher order aberrations with wavefront measuring devices such as disclosed in Williams U.S. Pat. No. 5,777,719 (incorporated herein by reference in its entirety), which describes an aberrometer instrument incorporating a Hartmann-Shack wavefront sensor to quantify higher order aberrations in the eye. The diagnostic measurement of higher order aberrations has lead to the ongoing development of systems and methods for customized ablation of the cornea and lenses used in or on the eye. The goal of customized ablation is to provide ever increasing visual quality in terms of acuity and contrast sensitivity (sometimes referred to as supernormal vision), as well as consistent image quality.

The technical advances in diagnostic equipment and treatment systems including lasers and eye trackers have also increased the accuracy required in making the diagnostic measurements and performing the treatments which are guided by these measurements. For example, it is desirable to obtain a diagnostic wavefront measurement of a patient's eye when the eye's pupil is dilated. Certain of the higher order aberrations that are suspected to cause glare or halos at night manifest themselves in the dilated (dark adapted) pupil. Therefore, a wavefront measurement with a wavefront sensing instrument is performed in a darkened environment such that the patient has a naturally dilated pupil. The measurement of the wavefront aberrations of the eye is obtained with respect to a reference point which is typically the pupil center or alternatively, a visual axis aligned to a fixation target in the diagnostic device. At the laser treatment stage, however, the nature and amount of light striking the eye from light sources in the treatment system environment typically causes the pupil to constrict. A complication arises because the center location of the dilated pupil is shifted from the center location of the constricted pupil. Thus, a calculated laser treatment centered on the constricted (treatment) pupil, based upon a diagnostic measurement aligned to the center of the dilated pupil, is likely to be applied at an incorrect location on the cornea.

Another complication arises from the fact that the position of a patient's eye in a sitting position rotates about an axis when the patient is in a treatment (supine) position. This is problematic because customized ablation treatment for higher order aberrations is not necessarily symmetric about an axis over the corneal surface. Moreover, a patient's head may have rotated between two diagnostic or eye image measurements separated in time, resulting in potential misalignment of a laser treatment. As such, both a translation and rotation of the eye must be accounted for between the diagnostic evaluation of the eye and the treatment stage.

One technique being developed to address these issues is referred to as iris pattern recognition. Rotation of the eye, for example, can sometimes be measured by identifying iris patterns using markers (artificial) or landmarks (natural). Since each person's iris is as unique as their fingerprints, it is proposed that various iris landmarks can be used to identify changing eye orientation. The reader is referred to the web site addresses: http://www.iriscan.com and http://schorlab.berkeley.edu for further information about iris pattern identification and eye movement. Notwithstanding that iris landmarks remain constant over the lifetime of the individual, it has been found that often the change in pupil size between diagnostic evaluation (dilated) and the treatment phase (constricted) is sufficient to deform or otherwise obscure the landmark, making it undetectable by conventional iris recognition software between diagnostic evaluation and treatment. Since it is highly desirable to be able to align the photoablative treatment of the cornea or other eye sites with the diagnostic measurement reference upon which it is based, there is a recognized need for methods and apparatus to acquire and maintain accurate alignment. A solution is proposed in applicant's co-pending patent application PCT/EP00/10373 which is incorporated herein in its entirety. That application discusses associating an artificially applied marker with diagnostic stage and therapeutic stage iris images in order to align these images at treatment. Thermal and dye based marks, for example, are suggested as artificial markers. It is appreciated, however, that patient discomfort, efficiency and accuracy are some disadvantages of current iris recognition and alignment means.

Accordingly, a need exists for devices, systems and methods to accurately account for the eye movement occurring between the diagnostic evaluation and treatment stages of laser eye surgery. The invention, while not limited as such, will be discussed in relation to laser vision correction such as LASIK, for example.

SUMMARY OF THE INVENTION

The invention is directed to apparatus and methods for aligning diagnostic and treatment images of a patient's eye in the absence of consistent parameters of the eye at the diagnostic evaluation stage and the treatment stage, in order to obtain improved results from laser vision correction surgery.

In an embodiment of the invention, an improvement is described for aligning a diagnostic iris image of a patient's eye with a treatment iris image of the patient's eye via iris pattern recognition. In a method wherein a diagnostic iris image of a patient's eye having a dilated pupil is attempted to be aligned with a treatment iris image of the eye having a constricted pupil, where it is attempted to identify an iris recognition landmark in the dilated pupil diagnostic iris image with the corresponding iris landmark in the constricted pupil treatment iris image, but due to deformation of the iris landmark associated with the change in pupil size, those corresponding landmarks cannot be identified for use as naturally occurring alignment markers in the iris, in order to accurately align a calculated laser treatment that is derived from a diagnostic measurement associated with the dilated pupil, the improvement is characterized by obtaining a sequential plurality of diagnostic iris images including a dilated pupil, a constricted pupil, and selected intermediate pupil sizes by capturing diagnostic images of the iris when it is illuminated by controlled amounts of visible illumination. Each of the sequential diagnostic iris images will contain at least an indicia of the iris recognition landmark such that in going from a dilated pupil to a constricted pupil in sequential steps, the landmark can be tracked from the dilated pupil image to the constricted pupil image. A diagnostic measurement of the patient's eye, preferably including a direct wavefront aberration measurement or a diagnostic measurement from which wavefront aberration data can be derived, is also obtained with the eye having a dilated or dark adapted pupil condition. An iris image of the patient's eye immediate prior to treatment, or a real time image is also obtained and due to environmental conditions in the treatment stage, the treatment iris image includes a constricted pupil. By tracking the iris recognition landmark through the series of diagnostic iris images from the dilated pupil condition upon which the diagnostic measurement and the laser treatment is based to the constricted pupil condition, the treatment iris image can be aligned with the resultant constricted pupil diagnostic image by matching and/or correlating the iris recognition landmark between the two constricted pupil images. In an aspect of this embodiment, the tracking and correlation of the diagnostic iris images can be accomplished by processing electronics and software in a treatment phase, and a resultant aligned diagnostic image can be exported to the laser treatment system where appropriate processing hardware and software can align the treatment iris image with the diagnostic iris image and adjust the laser treatment pattern accordingly. In an alternative aspect, the entire plurality of diagnostic iris images can be exported to the laser treatment system where appropriate processing hardware and software can align a treatment iris image with the corresponding pupil size diagnostic iris image via iris landmark identification. It will be appreciated by those skilled in the art that the export of diagnostic iris image data to the laser treatment system can be accomplished in a variety of ways including, but not limited to, land based or wireless telecommunications, computer storage media such as disk or CD, via the Internet or other networks, and so on. In a preferred aspect of the foregoing embodiment, a pupil translation is also used to ultimately adjust a laser treatment to the eye. This aspect is characterized by determining an illumination independent reference landmark on the eye, preferably a limbal edge, calculating a center position of the pupil with respect to the reference landmark wherein this calculation is performed with respect to the dilated pupil diagnostic iris image, making another center position calculation of the pupil with respect to the same reference landmark in relation to the constricted pupil diagnostic iris image, determining a vector displacement value for the constricted pupil center location and the dilated pupil center location, and therefrom adjusting the laser treatment to be performed on the constricted pupil eye with respect to the vector displacement of the dilated pupil center.

In another embodiment of the invention, an improvement is directed to a system for diagnostic and therapeutic laser eye treatment where it is intended to align a diagnostic iris image and a treatment iris image via iris pattern recognition techniques to effect a more accurate laser treatment, characterized in that the system includes a controllable, visible illumination component by which a controlled amount of visible illumination can be directed either to the patient's eye being examined or the patient's other eye (not being examined) with the effect of changing in a controlled way the pupil size of the eye under examination. A diagnostic image capture device is used to obtain a sequential plurality of diagnostic iris images, each having a different pupil diameter ranging between a dilated pupil size and a constricted pupil size corresponding to the level of controlled visible illumination. Although, as stated above, an iris recognition landmark present in both the dilated pupil diagnostic iris image and the constricted pupil diagnostic iris image cannot typically be tracked between these two image extremes, at least an indicia of the iris recognition landmark can be tracked through the sequential plurality of diagnostic iris images so that the dilated pupil diagnostic iris image can ultimately be correlated with the constricted pupil diagnostic iris image. The improved system further includes a diagnostic device for obtaining an appropriate diagnostic measurement of the patient's eye wherein this device is cooperatively associated with the illumination control device and the diagnostic image capture device. Further included is a means for exporting at least one of the diagnostic iris images to the laser treatment part of the system, and means for aligning the ultimate constricted pupil diagnostic iris image with the constricted pupil treatment image so that a more accurately positioned laser treatment can be applied to the eye. In an aspect of this embodiment, the means for aligning the plurality of diagnostic iris images and aligning an ultimate diagnostic image with the treatment iris image includes processing hardware and software associated with the treatment part of the system. In an alternative aspect, the alignment means includes processing hardware and software associated with the diagnostic part of the system for sorting and correlating the diagnostic iris images and processing hardware and software associated with the treatment part of the system for aligning the diagnostic iris image and the treatment iris image and, if desired, for adjusting the laser treatment itself. In a preferred aspect of the embodiment, the illumination control device includes a variable illumination fixation target that is an integrated component of the diagnostic measuring device. The image data export means can be any well-recognized method and apparatus for transmitting data from one site to another site, as described in connection with the first disclosed embodiment. In a preferred aspect, the improvement is further characterized by a means for obtaining a vector displacement measurement between the dilated pupil center associated with the dilated pupil diagnostic iris image and the pupil center of the constricted pupil diagnostic iris image. The means more preferably include a limbus landmark referencing to obtain the vector displacement.

In another embodiment, an improved ocular diagnostic device that provides measurement information indicative of or directly of wavefront aberration of the eye, and an iris image of the patient's eye associated with the diagnostic measurement, in which such an instrument typically includes diagnostic measurement components, an iris image capture component, and a visible illumination fixation source, is characterized by the fixation source having a controllable visible illumination level that will effect a controllable change in the pupil size of the eye being examined. A preferred improved diagnostic instrument is an aberrometer incorporating the controllable illumination fixation source. Alternatively, a corneal topographer can be adapted to include a controllable visible illumination fixation source or, a pupilometer can be adapted to incorporate the appropriate components for providing wavefront aberration data of the patient's eye.

These and other objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

DETAILED DESCRIPTION OF THE INVENTION

While the present invention is described with reference to illustrative embodiments for particular applications, it should be understood that the present invention is not so limited. Those having ordinary skill in the art and access to the teachings provided herein will recognize additional modifications, applications, and embodiments within the scope thereof and additional fields in which the invention will be of significant utility without undue experimentation.

The invention is directed to methods and systems providing alignment between diagnostic images of the eye and treatment images of the eye that result in greater accuracy of the laser treatment and, therefore, greater patient satisfaction.

An embodiment of the invention is described below in accordance with FIGS. 1 and 2. Systems and devices are known which use iris pattern recognition for identifying eye structures and for aligning diagnostic and therapeutic images for eye surgery. For example, PCT/EP00/10373 discusses systems and methods for alignment and photorefractive treatment of an eye in which a diagnostic iris image identified with artificial markers is obtained by a camera system along with a refractive diagnostic measurement. A computer system linked to the laser treatment system then uses this iris image information to develop and align the photorefractive treatment.

Figure 1:
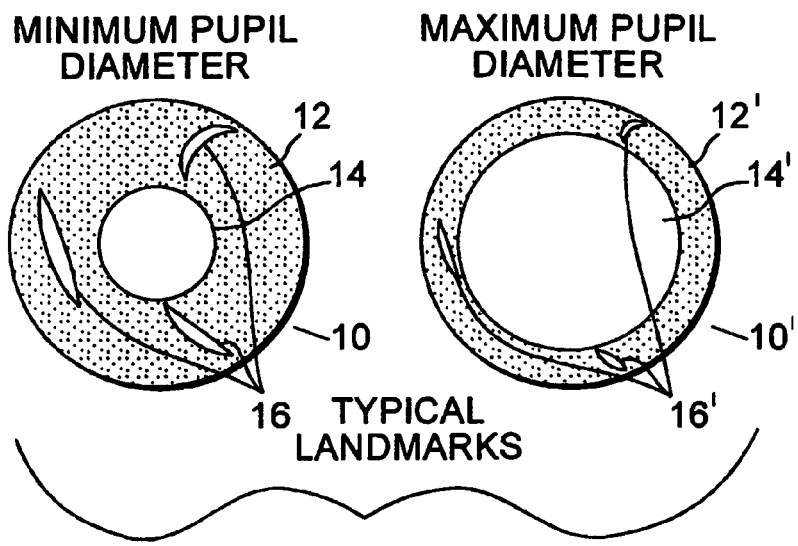
FIG. 1 is an illustration of two iris images having a constricted pupil and a dilated pupil, respectively, showing the change in form, position and size of naturally occurring landmarks at the two pupil diameter extremes.
Figure 2:
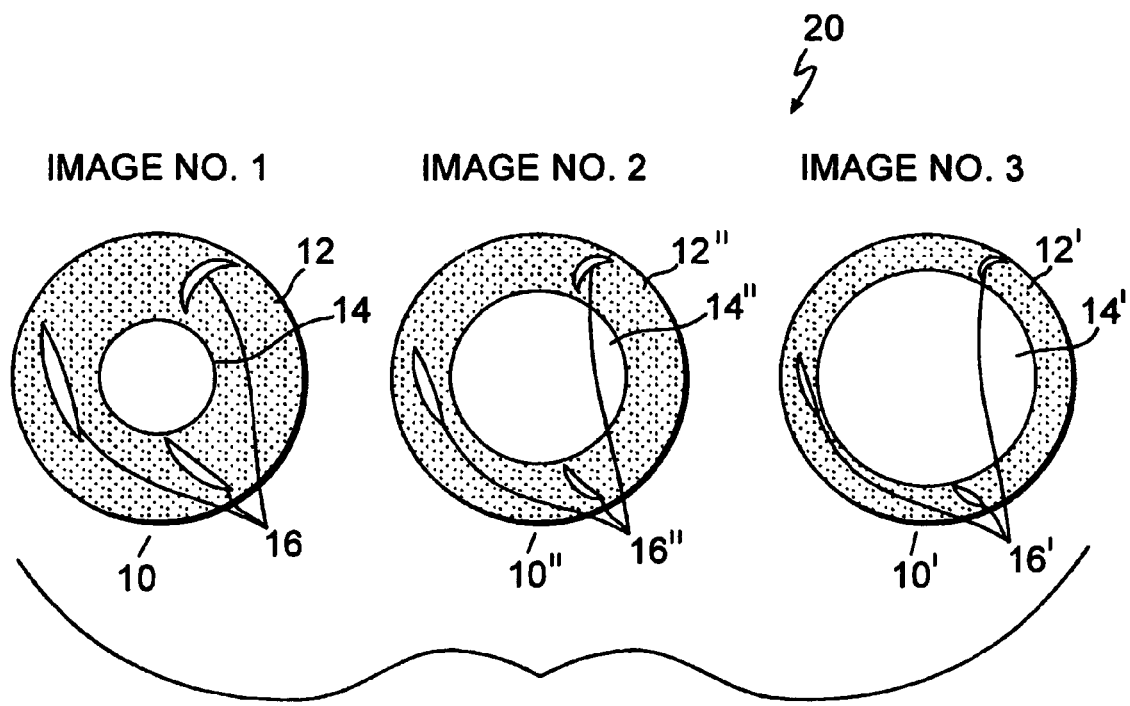
FIG. 2 schematically shows three sequential iris images having varying pupil diameters and the respective iris landmarks.

FIG. 1 schematically shows two sequential iris images 10', 10. Image 10 shows an iris area 12, a constricted pupil 14 and typical iris landmarks 16. For the purpose of the description of the invention, the term "constricted pupil" refers to a substantially small pupil size caused by bright light conditions, e.g., eye tracker and fixation light sources along with other environmental conditions present during the treatment phase of laser eye surgery that cause the pupil to constrict. The term constricted pupil, therefore, is not intended to merely describe the smallest possible pupil size that can be induced in a patient's eye, but to describe the smallest working pupil size in accordance with the invention. Iris image 10' shows the same iris 12', however the pupil 14' is dilated and the iris landmarks 16' are shown somewhat obscured due to the dilation of the pupil with respect to iris image 10. The dilated pupil 14', for the purpose of the description of the invention, is due to low light conditions typically associated with diagnostic measurement of the eye, for example, when a wavefront measuring device such as a Zywave™ (Bausch & Lomb/Technolas, Munich, Germany) wavefront measuring device or an Orbscan II® (Orbtek, Salt Lake City, Utah) corneal topographer is used to obtain wavefront aberration information. Thus, the term "dilated pupil" is not intended to refer merely to a maximally dilated pupil that is chemically or artificially induced, but rather to a dark adapted pupil, which is the largest working pupil size associated with this invention. The iris images 10, 10' in FIG. 1 are intended to illustrate the changes in form, position and size of naturally occurring landmarks 16, 16' when pupil size changes dramatically (e.g., from dilated to constricted). Under these circumstances, current iris pattern recognition technology has fallen short of being able to match landmark 16 in the constricted pupil condition with landmark 16' in the dilated pupil condition. Therefore, artificial markers on the eye have been used as in tracking points.

According to the invention, an improvement is described with reference to FIG. 2 as follows. In the diagnostic phase of laser vision surgery, a patient's wavefront aberration is measured. Wavefront measurements are typically centered about the patient's visual axis or about the center of the patient's dilated pupil. It is advantageous to measure the wavefront aberration over the dilated pupil because certain higher order aberrations manifest their vision compromising effects when the pupil is dark adapted (e.g., night time vision). Iris image 10' schematically shows the patient's iris image during diagnostic measurement, having a dilated pupil 14' and iris landmarks 16'. By controlling the visible illumination to either the patient's eye undergoing examination or the patient's other eye (not undergoing examination), preferably via a variable illumination fixation target in the diagnostic evaluation device, the pupil diameter of the eye being examined can be controlled. With reference to FIG. 2, a diagnostic iris image 10' is obtained by a diagnostic iris image capture device with the image 10' corresponding to the pupil diameter during the diagnostic evaluation. The visible illumination level is increased, causing a corresponding decrease in pupil diameter illustrated by 14" in iris image 10". Iris landmarks 16" are also visible having undergone a lesser change than shown in images 10', 10 of FIG. 1. As the illumination level is further increased, another diagnostic iris image 10 is obtained which shows a constricted pupil 14 and iris landmarks 16 which, again, have undergone a small and detectable change from landmarks 16" in iris image 10".

In this case, the pupil diameter 14 shown in diagnostic iris image 10 will substantially correspond to the pupil diameter of a treatment iris image obtained by a treatment iris image capture device during the treatment phase of the laser vision correction surgery. Diagnostic iris image processing hardware and software can now track the changes in the sequential set of iris images 10', 10'', 10 by tracking the landmark indicia so that the iris image 10' associated with the dilated diagnostic pupil 14' can be aligned with the iris image 10 associated with the constricted diagnostic pupil 14. Iris image processing hardware and software connected to a treatment part of the laser system is now used to align a treatment iris image, substantially represented by iris image 10 in FIG. 2, with the exported diagnostic iris image 10, allowing the laser ablation treatment pattern directed to the constricted treatment pupil to be accurately aligned with respect to the diagnostic iris image associated with the dilated diagnostic pupil. An advantage of this embodiment wherein the diagnostic iris images are sorted and aligned by the diagnostic stage processing results in the limited data transfer of a single image from the diagnostic phase to the treatment phase.

Since it is known that the rotational orientation of an eye changes when a patient moves from a sitting position to a supine position, the alignment method according to the invention provides appropriate information for rotating the laser ablation treatment pattern to correspond to the cyclorotation of the eye. A diagnostic measurement of the patient's eye in the dilated pupil condition is obtained in addition to the diagnostic iris images with the dilated through constricted pupil. As such, the image acquiring apparatus and the diagnostic measurement device may be separate devices, or, these functions may be integrated into a single device. Ultimately a diagnostic measurement will be used by the treatment laser system to calculate the appropriate ablation profile for vision correction. Therefore, it is preferable that the dilated diagnostic measurement be simultaneously associated with the dilated pupil diagnostic iris image. The diagnostic measurement itself will advantageously include the patient's wavefront aberration information which can be directly obtained by a variety of wavefront sensor instruments. One such device is the Zywave wavefront analyzer (Bausch & Lomb/Technolas) which incorporates a Hartmann-Shack wavefront sensor. Other types of devices such as elevation based topographers with ray trace capability such as, e.g., Orbscan II® corneal topography device (Bausch & Lomb/Orbtek, Salt Lake City, Utah) can provide measurement data from which wavefront aberration information can be derived. The diagnostic measurement also preferably includes a measure of the astigmatism.

In an aspect of this embodiment, the entire plurality of diagnostic iris images can be exported to the treatment stage processor where the diagnostic iris images can be sorted and appropriately aligned for correlation with the treatment iris image. This aspect would allow tracking and alignment of the treatment iris image in real time with a corresponding diagnostic iris image during the course of surgery. Due to the volume of information being transported between the diagnostic image processor and the treatment image processor, considerably more processing power may be required than for an alternative aspect in which the sorting and alignment of the dilated pupil and constricted pupil iris images is performed by a diagnostic image processor which then exports the aligned constricted pupil image to the treatment image processor for correlation and alignment with the treatment iris image. In this aspect, the computing power requirement is reduced at the expense of a static image comparison with the treatment iris image. A variety of factors will ultimately determine which aspect is preferred by the practitioner.

Figure 3:
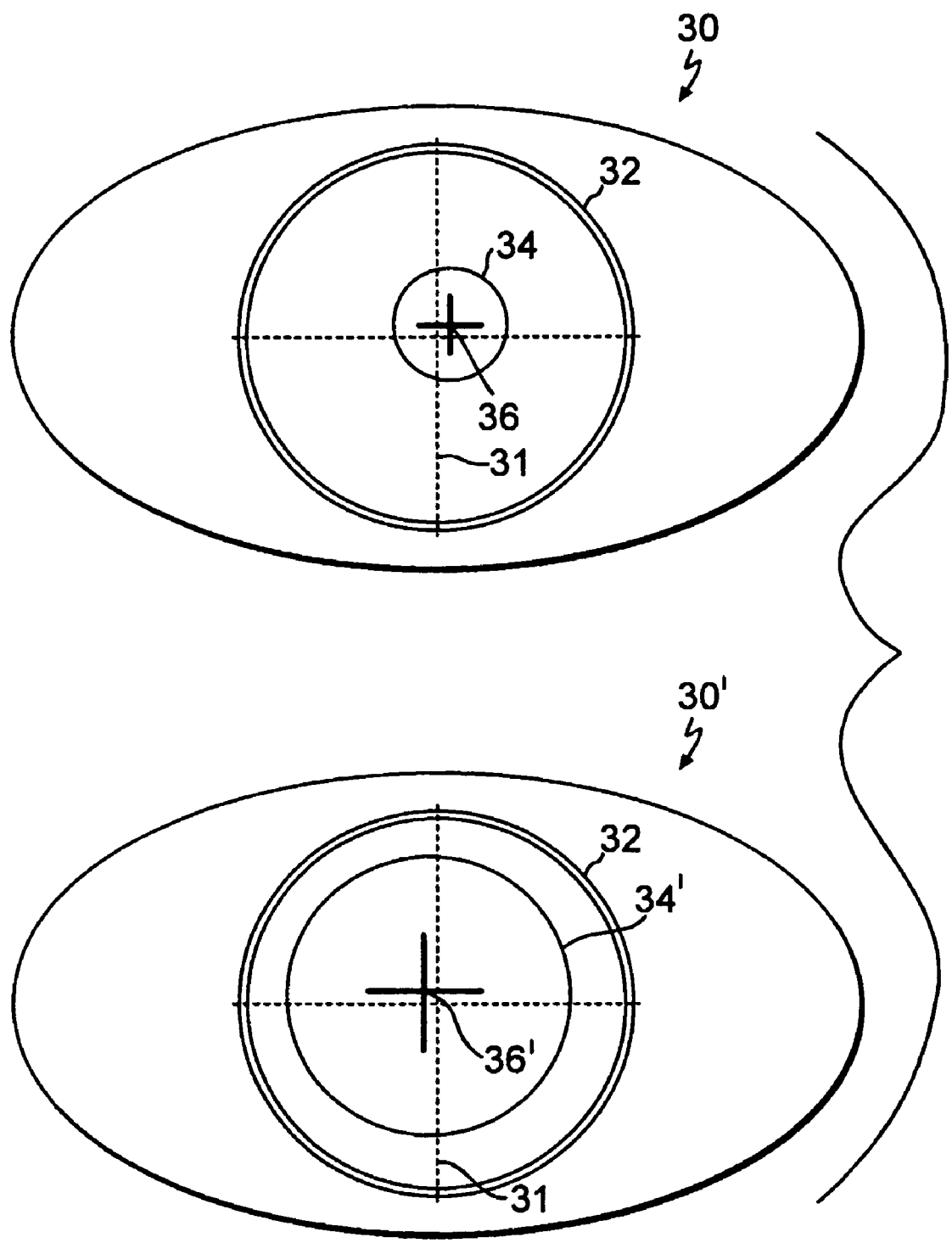
FIG. 3 schematically illustrates pupil center displacement with respect to a limbal reference as a function of different pupil sizes.

While the above alignment method provides an improved iris pattern recognition method for rotational adjustment of a laser treatment pattern, it will be appreciated that it is advantageous to translationally adjust the laser treatment pattern due to the translational shift that occurs in pupil center locations between a dilated pupil and a constricted pupil. With reference to FIG. 3, a diagnostic image 30' of the patient's eye having a dilated pupil 34' is obtained. A center location 36' of the dilated pupil 34' is determined with respect to an illumination independent eye landmark, preferably an edge of the limbus 32 of the patient's eye. Algorithms and mathematical means for calculating a center location of a pupil with respect to a radial reference point are well known by persons skilled in the art and require no explanation for carrying out the invention. A selected amount of visible illumination is directed to the eye to constrict the pupil as shown in eye image 30 by pupil 34. The center location 36 of the constricted pupil 34 is determined with respect to the eye landmark 32 which is the same as eye landmark 32 in image 30'. The limbal edge provides an advantageous reference point because the limbus is substantially unaffected by changes in pupil size. The vector displacement of the dilated pupil center 36' and the constricted pupil center 36 is determined by techniques well known to those skilled in the art. This vector displacement is then used to adjust the position of a calculated laser ablation treatment profile to be applied to the eye having a constricted pupil based upon diagnostic wavefront information obtained from the diagnostic image of the eye having a dilated pupil. It is advantageous to obtain the diagnostic images of the patient's eye and the measurement of the displacement of the center location of the pupil in infra red light so that pupil size does not change during this data acquisition. Once the vector displacement of the pupil centers is determined, this information can be saved in a treatment file of a controller of a treatment laser for use at an appropriate time.

Figure 4:
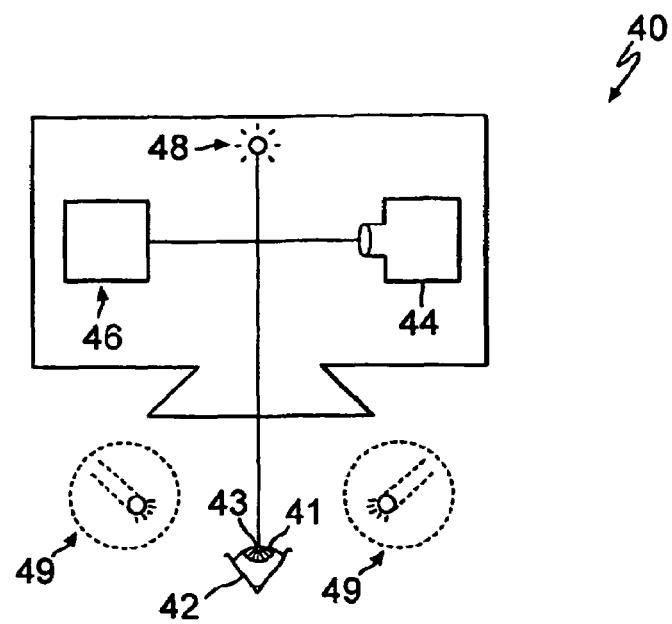
FIG. 4 is a schematic illustration of a device according to an embodiment of the invention.

With reference to FIG. 4, an improved diagnostic device 40 is described. In a preferred embodiment, device 40 is an aberrometer such as that described in Williams id, for obtaining a wavefront aberration measurement of a patient's eye 42. An iris 41 and a pupil 43 of the eye 42 are also shown. The aberrometer 40 typically contains an IR camera 44 for obtaining diagnostic images such as those schematically shown in FIGS. 1 and 2, a wavefront sensor and associated optics and electronics schematically represented by numeral 46 in FIG. 4, and a fixed illumination level fixation target 48 used for alignment purposes as well understood by those skilled in the art. According to the invention, the improvement comprises replacing fixed illumination fixation target 48 with a variably controllable visible illumination fixation target so that the diameter of the pupil 43 of the patient's eye can be changed to obtain the diagnostic iris images as described herein above. In an alternative aspect of this embodiment illustrated by the dotted line inserts 49 in FIG. 4, the controllable visible illumination source can be externally associated with the device 40 as represented by controllable visible illumination sources 49.

Alternatively, (not shown) the device 40 could be a corneal topographer such as an Orbscan II device adapted with a controllable visible illumination source as described herein. Likewise, device 40 could be a pupilometer typically including a controllable visible illumination source for pupil diameter control with the improvement according to the invention being a wavefront sensing component or other known hardware and software components that would provide wavefront aberration information about the eye under examination.

Figure 5:
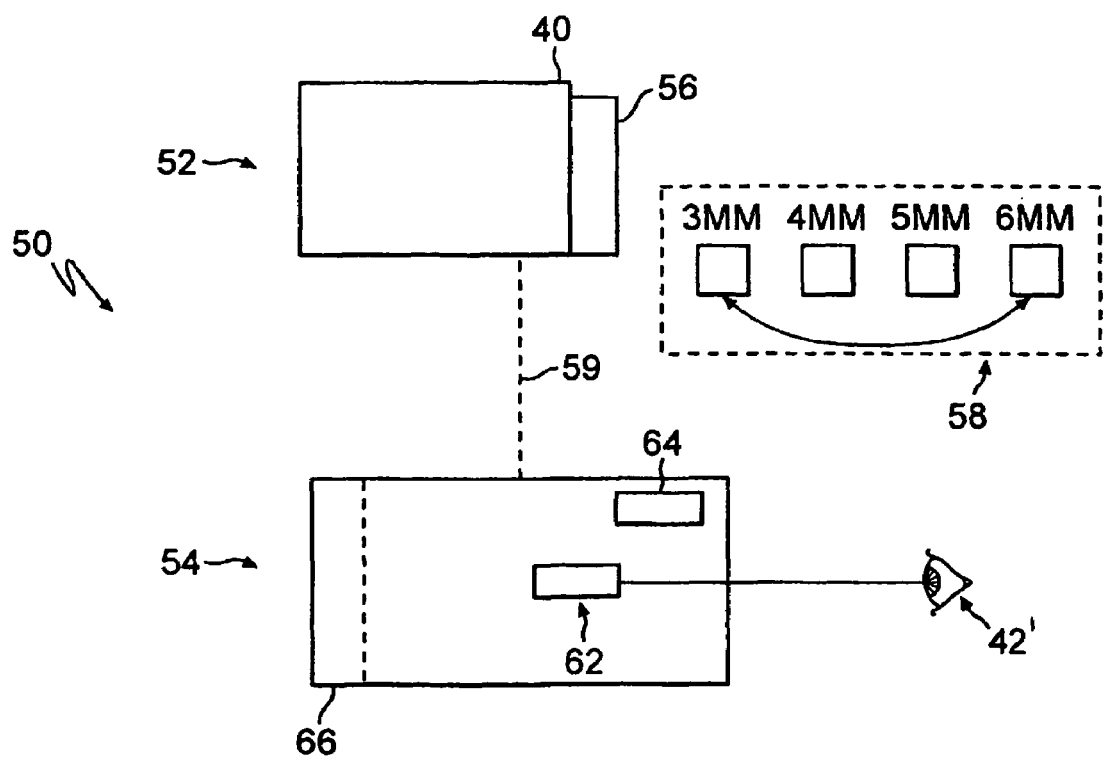
FIG. 5 is a schematic illustration of a system according to an embodiment of the invention.

A system embodiment according to the invention is described with respect to FIG. 5. The system 50 is a diagnostic and therapeutic system for laser eye surgery that includes a diagnostic part 52 and a laser treatment part 54. The diagnostic part 52 includes a diagnostic instrument 40 as described with respect to FIG. 4 and a diagnostic processor 56 that is programmed to sort, correlate and align the diagnostic iris images as represented in 58. An ultimately aligned constricted pupil diagnostic iris image (as described herein above) is exported from diagnostic part 52 as illustrated by reference 59 via any variety of well-known image data transfer means including land based and wireless communications, computer storage media such as disk or CD, via the Internet or other networks, etc., to laser treatment part 54. Laser treatment part 54 includes a treatment iris image capture device 64 for obtaining the treatment iris image having a constricted pupil of eye 42', a treatment laser 62 and other components such as an eye tracker (not shown). In an alternative aspect of this embodiment, the entire plurality of diagnostic iris images as represented at 58 is exported to treatment part 54 where processing hardware and software represented by processor 66 sorts and correlates the diagnostic iris images and provides the appropriate alignment between the constricted pupil treatment image and the corresponding constricted pupil diagnostic iris image. Processor 66 may also control the calculated laser ablation pattern in response to the iris pattern recognition alignment.

In some cases, it may be preferable to have a processor 56 in the diagnostic part 52 and a processor 66 in the treatment part 54, however the nature and location of the processing hardware and software will be determined by surgeon preference and available iris recognition software and hardware components.

In a preferred aspect of the system embodiments described herein, the processor 56 associated with diagnostic instrument 40 is adapted to calculate a vector displacement of the pupil center between the dilated pupil diagnostic image and the constricted pupil diagnostic image. This information is likewise exported to the laser treatment part 54 of the system 54 to be used for translationally adjusting the laser treatment pattern on the treatment eye which has a constricted pupil.

The foregoing embodiments of the invention can be illustrated by example as follows: A patient is seated and aligned with respect to a diagnostic device (e.g., aberrometer) that can provide a diagnostic wavefront measurement of the patient's eye and which can acquire and process diagnostic iris images. The patient's eye is aligned in respect f the aberrometer with the use of a low level visible illumination fixation target such that the patient's dark adapted pupil diameter might be in the range of 6 to 7 mm. Both a diagnostic wavefront measurement and a dilated pupil diagnostic iris image are obtained at this point. The brightness of the fixation target is then increased until the patient's pupil diameter decreases to about 5 mm. Another diagnostic iris image is obtained and stored. The illumination level of the fixation target is sequentially increased so that diagnostic iris images may be obtained at various pupil sizes until a constricted pupil (e.g., about 2 mm.) diagnostic iris image is obtained. A pupil center shift is also calculated in the form of a vector displacement for the dilated pupil diagnostic iris image and the constricted pupil diagnostic iris image through limbal edge detection. Processing hardware and software associated either with the diagnostic system and/or the treatment system tracks an iris recognition landmark through the different pupil sized diagnostic iris images to ultimately align the dilated pupil diagnostic image with the constricted pupil diagnostic iris image. An ablation profile is generated based upon the diagnostic measurement associated with the dilated pupil. The rotational alignment and vector displacement data is also made available to the treatment laser system. At some later time, the patient is positioned (supine) under the treatment system and a real time image of the actual constricted pupil/iris is obtained. This treatment iris image is then aligned with the substantially corresponding diagnostic iris image having generally the same pupil size via the identified iris recognition landmark, so that the calculated ablation treatment can be rotated, translated and otherwise adjusted to provide a more accurate treatment. In the event the iris pattern recognition software cannot detect an iris landmark that can be tracked with a high level of confidence, the limbus based pupil center displacement can be used at a minimum to eliminate decentration in spite of uncorrected rotation.

Although preferred embodiments of the present invention have been described in detail herein above, it should be clearly understood that many variations and/or modifications of the basic inventive concepts taught herein, which may appear to those skilled in the art, will still fall within the spirit and scope of the present invention as defined in the appended claims and their equivalents.

The invention claimed is:

1. A method for aligning a diagnostic iris image of a patient's eye having a dilated pupil with a treatment iris image of the eye having a constricted pupil, via an iris pattern recognition technique, wherein an iris recognition landmark in the dilated pupil diagnostic image is not directly identifiable with the corresponding iris recognition landmark in the constricted pupil treatment iris image, to effect an accurate laser treatment of the patient's eye that is derived from a diagnostic measurement associated with the dilated pupil, characterized by:

visibly illuminating the patient's eye with a plurality of selected levels of visible illumination to effect a corresponding plurality of different pupil sizes ranging from a constricted pupil diameter to a dilated pupil diameter;

respectively obtaining a sequential plurality of diagnostic iris images each of which has an indicia of the iris recognition landmark;

correlating the indicia of the iris recognition landmark in each sequential diagnostic iris image such that the iris recognition landmark in the constricted pupil diagnostic iris image is identifiable with the iris recognition landmark in the dilated pupil diagnostic iris image;

making a diagnostic measurement of the patient's eye and the associated diagnostic image when the pupil is dilated;

obtaining a treatment iris image of the patient's eye having a constricted pupil;

aligning the constricted diagnostic iris image with the constricted pupil treatment iris image.

2. The method of claim 1, further characterized by adjusting the laser treatment on the eye based upon the iris alignment.

3. The method of claim 1, wherein making the diagnostic measurement includes obtaining an indication of a wavefront aberration and an axis of astigmatism.

4. The method of claim 3, wherein making the diagnostic measurement comprises using one of an elevation based topographer, optical raytracing, and an aberrometer.

5. The method of claim 1, wherein the aligning comprises correlating the dilated pupil diagnostic iris image with the constricted pupil diagnostic iris image and comparing an aligned constricted pupil diagnostic iris image with the constricted pupil treatment image.

6. The method of claim 1, wherein the aligning comprises comparing the plurality of diagnostic iris images with the treatment iris image to align the constricted pupil diagnostic iris image with the constricted pupil treatment iris image.

7. The method of claim 1, wherein the laser treatment is directed to one of a myopia correcting ablation, a hyperopia correcting ablation, an astigmatism correcting ablation, a custom corneal ablation, a retinal ablation, and another laser eye surgery procedure.

8. The method of claim 1, further characterized by determining an illumination independent reference landmark on the eye;
  calculating a center position of the pupil with respect to the reference landmark associated with the dilated pupil diagnostic iris image;
  calculating a center position of the pupil with respect to the reference landmark associated with the constricted pupil diagnostic iris image;
  determining a vector displacement value for the constricted pupil center and the dilated pupil center;
  adjusting the laser treatment to be performed on the constricted pupil eye with respect to the vector displacement of the dilated pupil center.

9. The method of claim 8, wherein the illumination independent reference landmark is a portion of the limbus of the eye.

10. The method of claim 9, wherein the portion of the limbus is a limbal edge.

11. In a diagnostic and therapeutic system for laser eye surgery wherein a diagnostic image of a patient's eye that is obtained by a diagnostic image capture is aligned with a treatment image of the patient's eye that is obtained by a treatment image capture device that is associated with a treatment laser system, via an iris pattern recognition technique, the improvement characterized by:
  an illumination control device for controlling a visible illumination level on one of the patient's eye being examined and the patient's other eye, not being examined, wherein the visible illumination level acts as a control for the pupil diameter of the examined eye;
  a sequential plurality of diagnostic iris images each including a different pupil diameter ranging between a dilated pupil size and a constricted pupil size corresponding to the controlled visible illumination level, wherein at least an indicia of an iris recognition landmark is identifiable in each sequential diagnostic iris image even though the corresponding iris recognition landmark is not identifiable between the constricted diagnostic pupil image and the dilated diagnostic pupil image;
  an eye diagnostic measuring device for obtaining a diagnostic measurement of the patient's eye associated with the dilated diagnostic pupil image, cooperatively associated with the illumination control device and the diagnostic image capture device;
  means for exporting at least one of the diagnostic iris images to the laser treatment system; and
  means for aligning the dilated pupil diagnostic iris image with the constricted pupil diagnostic iris image, and further for aligning the aligned constricted pupil diagnostic iris image with the treatment iris image having a constricted pupil of a size generally corresponding to the diagnostic image constricted pupil size.

12. The system of claim 11, wherein the means for aligning includes a treatment stage processor cooperatively engaged with the treatment image capture device.

13. The system of claim 11, wherein the means for exporting includes at least one of a wired connection, a wireless connection, a computer file storage medium.

14. The system of claim 11, wherein the diagnostic measurement obtained by the eye diagnostic measuring device is suitable for obtaining a wavefront information about the patient's eye.

15. The system of claim 11, wherein the eye diagnostic measuring device includes the iris image capture device.

16. The system of claim 11, wherein the illumination control device is separate from the diagnostic measuring device.

17. The system of claim 11, wherein the illumination control device comprises a variable illumination fixation target and is an integrated component of the diagnostic measuring device.

18. The system of claim 11, wherein the improvement is further characterized by a means for obtaining a vector displacement measurement between a pupil center of the dilated pupil diagnostic image and the pupil center of the constricted pupil diagnostic image.

19. The system of claim 18, wherein the vector displacement measurement is a measurement from limbus reference position to the center of the pupil.

20. In a diagnostic and therapeutic system for laser eye surgery wherein a diagnostic image of a patient's eye that is obtained by a diagnostic image capture device that is also adapted to make a diagnostic measurement of the patient's eye, is aligned with a treatment image of the patient's eye that is obtained by a treatment image capture device which is associated with a treatment laser system, via an iris pattern recognition technique, the improvement characterized by:
  an illumination control device for controlling a visible illumination level on one of the patient's eye being examined and the patient's other eye, not being examined, wherein the visible illumination level acts as a control for the pupil diameter of die examined eye;
  a sequential plurality of diagnostic iris images each including a different pupil diameter ranging between a dilated pupil size and a constricted pupil size corresponding to the controlled visible illumination level, obtained by the diagnostic image capture device, wherein an iris recognition landmark is identifiable in each sequential diagnostic iris image even though the corresponding iris recognition landmark is not identifiable between the constricted diagnostic pupil image and the dilated diagnostic pupil image;
  means for exporting at least one of the diagnostic iris images to the laser treatment system;
  means for aligning the dilated pupil diagnostic iris image, associated with a diagnostic measurement image, with the constricted pupil diagnostic iris image; and
  means for aligning the aligned constricted pupil diagnostic iris image with the treatment iris image having a constricted pupil of a size generally corresponding to the diagnostic image constricted pupil size.

21. The system of claim 20, wherein the means for aligning the dilated pupil diagnostic iris image with the constricted pupil diagnostic iris image includes a diagnostic stage processor cooperatively engaged with the diagnostic image capture device.

22. The system of claim 21, wherein the means for exporting includes at least one of a wired connection, a wireless connection, a computer file storage medium.

23. The system of claim 20, wherein the diagnostic measurement obtained by the eye diagnostic measuring device is suitable for obtaining a wavefront information about the patient's eye.

24. The system of claim 20, wherein the eye diagnostic measuring device includes the iris image capture device.

25. The system of claim 20, wherein the illumination control device is separate from the diagnostic measuring device.

26. The system of claim 20, wherein the illumination control device comprises a variable illumination fixation target and is an integrated component of the diagnostic measuring device.

27. The system of claim 20, wherein the improvement is further characterized by a means for obtaining a vector displacement measurement between a pupil center of the dilated pupil diagnostic image and the pupil center of the constricted pupil diagnostic image.

28. The system of claim 21, wherein the vector displacement measurement is a measurement from limbus reference position to the center of the pupil.

* * * * *